US011691930B2

United States Patent
Nesterenko et al.

(10) Patent No.: US 11,691,930 B2
(45) Date of Patent: *Jul. 4, 2023

(54) PROCESS FOR CONVERTING ONE OR MORE METHYL HALIDES TO ACYCLIC C3-C6 OLEFINS

(71) Applicants: TOTALENERGIES ONETECH, Courbevoie (FR); SULZER MANAGEMENT AG, Winterthur (CH)

(72) Inventors: Nikolai Nesterenko, Nivelles (BE); Gleb Veryasov, Nivelles (BE); Raoul Dethier, Schaerbeek (BE)

(73) Assignees: TOTALENERGIES ONETECH, Courbevoie (FR); SULZER MANAGEMENT AG, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/777,865

(22) PCT Filed: Nov. 20, 2020

(86) PCT No.: PCT/EP2020/082835
§ 371 (c)(1),
(2) Date: May 18, 2022

(87) PCT Pub. No.: WO2021/099543
PCT Pub. Date: May 27, 2021

(65) Prior Publication Data
US 2022/0356128 A1  Nov. 10, 2022

(30) Foreign Application Priority Data

Nov. 22, 2019 (EP) ..................................... 19315142

(51) Int. Cl.
| | |
|---|---|
| *C07C 1/30* | (2006.01) |
| *B01J 29/70* | (2006.01) |
| *B01J 35/10* | (2006.01) |
| B01J 37/10 | (2006.01) |
| B01J 37/00 | (2006.01) |
| B01J 37/02 | (2006.01) |
| B01J 35/00 | (2006.01) |
| B01J 37/28 | (2006.01) |

(52) U.S. Cl.
CPC .................. *C07C 1/30* (2013.01); *B01J 29/70* (2013.01); *B01J 29/7015* (2013.01); *B01J 35/1057* (2013.01); B01J 35/006 (2013.01); B01J 37/0009 (2013.01); B01J 37/0201 (2013.01); B01J 37/10 (2013.01); B01J 37/28 (2013.01); B01J 2229/42 (2013.01); C07C 2529/70 (2013.01)

(58) Field of Classification Search
CPC ......... C07C 1/26; C07C 1/30; C07C 2529/70; C07C 2529/84; C07C 2529/85; B01J 29/70; B01J 29/84; B01J 29/85; B01J 35/1057; B01J 35/006; B01J 37/0009; B01J 37/0201; B01J 37/10; B01J 37/28; B01J 2229/42; B01J 29/7015
USPC .................................................. 585/640, 641
See application file for complete search history.

(56) References Cited

U.S. PATENT DOCUMENTS

| | | | |
|---|---|---|---|
| 7,307,196 B2 * | 12/2007 | Levin ........................ | C07C 1/20 585/641 |
| 2008/0188701 A1 | 8/2008 | Qi et al. | |
| 2017/0057886 A1 | 3/2017 | Fickel | |

FOREIGN PATENT DOCUMENTS

WO        2016099775 A1     6/2016

OTHER PUBLICATIONS

International Search Report and Written Opinion issued in Application No. PCT/EP2020/082835 dated Jan. 26, 2021; 10 pages.

* cited by examiner

*Primary Examiner* — Elizabeth D Wood
(74) *Attorney, Agent, or Firm* — Ewing & Jones, PLLC (57) ABSTRACT

The present disclosure relates to a process for converting one or more methyl halides to acyclic C3-C6 olefins, said process comprising the steps of (a) providing a feedstream comprising one or more methyl halides; (b) providing a catalyst composition; and (c) contacting said feedstream with said catalyst composition under reaction conditions. The process is remarkable in that said reaction conditions include a reaction temperature below 400° C., and in that said catalyst composition comprises one or more molecular sieves with a Si/Al atomic ratio ranging from 2 to 18 and wherein said one or more molecular sieves comprise a plurality of pores, wherein said pores have a shape of an 8-membered ring or less.

23 Claims, 2 Drawing Sheets

PROCESS FOR CONVERTING ONE OR MORE METHYL HALIDES TO ACYCLIC C3-C6 OLEFINS

CROSS-REFERENCE TO RELATED APPLICATIONS

This application claims the benefit of PCT/EP2020/082835 filed Nov. 20, 2020, which claims priority from EP 19315142.0 filed Nov. 22, 2019, which are incorporated herein by reference in their entireties for all purposes.

TECHNICAL FIELD

The present disclosure relates to a process for converting one or more methyl halides selectively into acyclic C3-C6 olefins.

TECHNICAL BACKGROUND

Olefins are used to make numerous downstream products. Starting from alkanes, and methane, in particular, it is feasible to obtain the corresponding alkyl halide, for example, methyl halide. Alkyl halide can be then transformed into olefins. By adjusting the reaction conditions and employing a specific catalyst, the ratios of these various olefins may be modified, leading to the obtaining of the desired effluents, that can be then separated by known technology. The process for converting mono-halogenoalkane into olefins, namely the second step of the two-step process for producing olefins from alkanes, has already been thoroughly studied.

Figure 1:
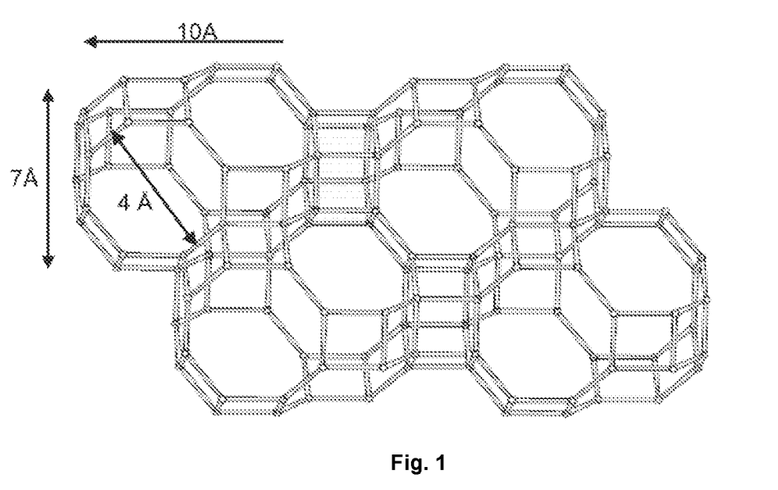
FIG. 1 shows the cage structure of molecular sieve having a chabazite structure according to the prior art.

In US 2017/0057886, an aluminosilicate small-pore zeolite catalyst, i.e. a chabazite zeolite of the SSZ-13 type, with a silicon to aluminium ratio (SAR) less than 100 to 1 and described as having a higher acidity than a silicoaluminophosphate catalyst (due to the presence of aluminium ions in the crystal structure instead of silicon atoms), has been used in the C2-C4 olefins production from chloromethane. The experiment was conducted in a fixed-bed tubular reactor at a temperature of 450° C. for about 10 hours, to obtain selectivity in ethylene of 34.95% and in propylene of 33.99% and conversion of 98.93%. A maximum selectivity to C4 olefins of 15% is described as well as a maximum selectivity to aromatics of 1%. Finally, no more than 2% of C2-C4 alkanes are produced. The SSZ-13 catalyst is described as having relatively small pore diameter and preventing, therefore, molecules larger than C4 hydrocarbons from exiting the zeolite framework. FIG. 1 shows a structure of the cages of a zeolite having chabazite structure, with an average pore diameter amounting to 4 Å. The main disadvantage of this approach is a fast deactivation of catalyst and significant production of ethylene together with high selectivity to coke, which is not even reported. These means that a significant amount of chloromethane is transformed to $CO_2$ during regeneration. These catalytic systems could be used only in a fluidized bed reactor.

In WO 2016/099775, the methyl chloride transformation into olefins was studied with a SAPO-34 zeolite catalyst. After 20 h on stream, a conversion of 90.7% was achieved and a good selectivity in ethylene (40.4%) and propylene (42.9%) were observed. However, it is well known that the SAPO based catalytic systems are very sensitive to the acid environment and in case of the presence of any HCl in the regeneration gases, it will result in irreversible catalyst deactivation. In the same time, a significant amount of the methyl chloride is transformed to coke and the reaction cycle is short.

US 2008/0188701 describes the use of a silicoaluminophosphate molecular sieve catalyst, which comprises 50 wt. % of SAPO-34 small-pore molecular sieve as active component and 50 wt. % of alumina as a matrix. At relatively low temperature (350° C.), 28.46% of methyl chloride was converted affording a selectivity in ethylene of 28.31%, in propylene of 42.08% and C4 olefins of 17.42%. At higher temperatures, the formation of ethylene is favoured. However, once again, it is well known that the SAPO based catalytic systems are very sensitive to the acid environment and in case of the presence of any HCl in the regeneration gases, it will result in irreversible catalyst deactivation.

The description of the prior art shows that small-pore zeolites, such as zeolite having a chabazite (CHA) structure, convert an alkyl halide into light olefins, especially C2 to C3 olefins and suffer from fast deactivation. One should mention that a significant amount of ethylene is formed with high selectivity to coke. So, the known small-pore catalyst systems known in the prior art are not very efficient for the transformation of methyl halides to C3-C6 olefins.

The present disclosure has for objective to provide a process wherein the conversion of methyl halides into olefins with a small-pore molecular sieve leads selectively to the formation of acyclic C3-C6 olefins (i.e. more than 75% of selectivity to C3-C6 olefins); preferably with reduced selectivity to ethylene (i.e. less than 15% of selectivity to ethylene) and with reduced selectivity to aromatics (i.e. less than 5% of selectivity to aromatics). In particular, the ethylene could be recycled back to the reactor to produce more C3-C6 olefins.

SUMMARY

According to a first aspect, the disclosure provides a process for converting one or more methyl halides to acyclic C3-C6 olefins, said process comprising the following steps:
a) providing a feedstream comprising one or more methyl halides;
b) providing a catalyst composition; and
c) contacting said feedstream with the said catalyst composition under reaction conditions;
the process is remarkable in that
said reaction conditions include a reaction temperature below 400° C., and in that said catalyst composition comprises one or more molecular sieves with a Si/Al atomic ratio ranging from 2 to 18, and wherein said one or more molecular sieves comprise a plurality of pores, wherein said pores have a shape of an 8-membered ring or less and further wherein one or more molecular sieves have an average pore size diameter of at most 4.2 Å, as determined by BET (Brunauer-Emmet-Teller) experiments.

In an embodiment, the one or more molecular sieves are selected from one or more silico aluminophosphates and/or one or more zeolites; preferably, the one or more molecular sieves are one or more zeolites.

Surprisingly, it has been found that the process for converting methyl halides to acyclic C3-C6 olefins provides a particularly high selectivity to acyclic C3-C6 olefins along with a low generation of ethylene and coke when the catalyst composition comprises molecular sieves with a Si/Al atomic ratio ranging from 2 to 18 or from 5 to 18 and comprises a plurality of pores, the biggest of said pores being an 8-membered ring. Moreover, the catalyst composition in the process of the present disclosure is highly stable. It was found that the use of molecular sieve having a Si/Al atomic ratio from 2 to 18 (SAR from 4 to 36) or having a Si/Al atomic ratio from 5 to 18 (SAR from 10 to 36) of a specific structure with pores having a shape of an 8-membered ring or less allows for steadily transforming methyl halides into acyclic C3-C6 olefins for at least 24 hours. Without wishing to be bound by any theory, a person having ordinary skill in the art will see a difference in the reaction mechanism observed on that system relative to the one described in the literature. All the known small molecular sieves showed the selectivity typical to the 'hydrocarbon pool' mechanism, which is well described in the literature. This disclosure shows that in case of using a particular molecular sieve with the optimal Si/Al atomic ratio, the transformation of a methyl halide ($CH_3X$) could be performed via oligo-dehydrohalogenation mechanism (homologation followed by subtraction of HX). The advantage of this reaction pathway is a very low formation of coke and high catalyst stability. The catalyst is suitable for the conventionally fixed bed operation and produced only a very little amount of ethylene.

The production of olefins higher than C4 is a surprising result of the disclosure as US2017/0057886 was teaching that the production of olefins higher than C4 was inhibited by the use of a small pore zeolite, i.e. a zeolite with a pore size inferior to 4 Å.

The group of AEI, CHA, DDR, ERI, KFI, and LEV families are molecular sieves comprising at least one cage and at least one channel, wherein said at least one cage and said at least one channel have each an opening, the opening of the cage being greater than the opening of the channel.

According to the disclosure the molecular sieves with a Si/Al atomic ratio ranging from 2 to 18 or from 5 to 18 with cage(s) bigger than channel(s) are selected from the group of AEI, CHA, DDR, ERI, KFI, and LEV families and any mixture thereof.

With preference, one or more of the following embodiments can be used to better define the catalyst composition used in the process:
- The one or more molecular sieves are exchanged with two-valent cations.
- The one or more molecular sieves are steamed. This allows the one or more molecular sieves of the catalyst composition to have a Si/Al atomic ratio ranging from 2 to 18 or from 5 to 18 or from 5 to 15.
- The one or more molecular sieves are exchanged with two-valent cations and steamed.
- The one or more molecular sieves are selected from the group of ABW, ACO, AEI, AEN, AFN, AFT, AFV, AFX, ANA, APC, APD, ATN, ATT, ATV, AVL, AWO, AWW, BCT, BIK, BRE, CAS, CDO, CHA, DDR, DFT, EAB, EDI, EEI, EPI, ERI, ESV, ETL, GIS, GOO, IFY, IHW, IRN, ITE, ITW, JBW, JNT, JOZ, JSN, JSW, KFI, LEV, LTA, LTJ, LTN, MER, MON, MRT, MTF, MWF, NPT, NSI, OWE, PAU, PHI, POR, RHO, RTE, RTH, RWR, SAS, SAT, SAV, SFW, SIV, SWY, THO, TSC, UEI, UFI, VNI, YUG, and ZON families and any mixture thereof. with preference, said one or more molecular sieves are selected from SSZ-39 of the AEI family, SSZ-13 of the CHA family, SSZ-16 of the AFX family, preferably, said one or more molecular sieves are selected from SSZ-39 of the AEI family, SSZ-13 of the CHA family, SAPO-35 of the LEV family and any mixture thereof; even more preferably, said one or more molecular sieves are selected from SSZ-39 of the AEI family.
- The preferred molecular sieve from the AEI family are one or more of SSZ-39, ALPO-18 or SAPO-18, more preferably is SSZ-39.
- The preferred molecular sieve from the CHA family are one or more of chabazite, SSZ-13, K-G, SSZ-62 or SAPO-34, SAPO-44, more preferably is SSZ-13.
- The preferred molecular sieves from the DDR family are one or more of ZSM-58 or Sigma-1.
- The preferred molecular sieves from the ERI family are one or more of erionite or UZM-12.
- The preferred molecular sieve from KFI family is ZK-5.
- The preferred molecular sieves from the LEV family are one or more of SAPO-35, levyne, ZK-20, SSZ-17 or NU-3.
- The preferred molecular sieve from the AFX family is SSZ-16.
- The one or more molecular sieves are selected from the group of AEI, CHA, DDR, ERI, KFI, and LEV families and any mixture thereof.
- The one or more molecular sieves are selected from SSZ-39 of the AEI family, SSZ-13 of the CHA family, SAPO-35 of the LEV family, preferably, said one or more molecular sieves are selected from SSZ-39 of the AEI family, SSZ-13 of the CHA family, and any mixture thereof; even more preferably, said one or more molecular sieves are selected from SSZ-39 of the AEI family
- The one or more molecular sieves have an average pore size diameter of at most 3.8 Å, as determined by BET (Brunauer-Emmet-Teller) experiments; preferably of 3.8 Å.
- The catalyst composition contains one or more alkaline earth metal-containing materials. Said one or more alkaline earth metal-containing materials are selected from the group of beryllium, magnesium, calcium, strontium, barium, and any mixtures thereof.
- The catalyst composition further comprises from 1 to 50 wt. % of hydrotalcite as based on the total weight of the catalyst composition; preferably from 5 to 25 wt. %, more preferably from 7 to 23 wt. %, even more preferably from 10 to 20 wt. %.
- The one or more molecular sieves after or before steaming are doped with one or more phosphorus-containing materials, to form a phosphate molecular sieve. With preference, said phosphate molecular sieve can be further subjected to a steaming step.
- The catalyst composition comprises between 0.1 wt. % and 7.0 wt. % of one or more phosphorus-containing materials as based on the total weight of the catalyst composition, preferably between 0.3 wt. % and 4.5 wt. %, preferentially between 0.5 wt. % and 4.0 wt. %, more preferentially 2.0 wt. %.
- The one or more molecular sieves are doped with one or more phosphorus-containing materials and with one or more alkaline earth metal-containing materials, preferably a magnesium or calcium-containing material.
- The catalyst composition further comprises a binder; with preference, said binder is one or more selected from the group of silica, alpha-alumina, clays, alumina phosphates, calcium phosphates, magnesium phosphates, and mullite; more preferentially, silica.
- The catalyst composition further comprises a binder, and the binder is present in an amount of at least 10 wt. % as based on the total weight of the catalyst composition; preferably in an amount of at least 20 wt. %, most preferably in an amount of at least 30 wt. %, even more preferably in an amount of at least 40 wt. %, and most preferably in an amount of at least 50 wt. %.

One or more molecular sieves are transition metal-free. With preference, the one or more molecular sieves contain less than 1000 wt. ppm of noble metal as determined by XRF and/or less than 1 wt. % of transition metals as determined by XRF based on the total weight of the one or more molecular sieves; with preference, the content of the transition metals is below 1.0 wt. %, preferably below 1000 wt.ppm based on the total weight of the one or more molecular sieves. Traces of these metals may be present on the catalyst as impurities from the binder, e.g. a component of the clays The one or more molecular sieves are alkali metal-free. With preference, the one or more molecular sieves contain less than 1 wt. % of alkali metals as determined by XRF based on the total weight of the one or more molecular sieves, more preferably below 0.5 wt. %.

At least 50 wt. % of said one or more molecular sieves are in their hydrogen form as based on the total weight of the one or more molecular sieves, preferentially at least 60 wt. %, more preferentially at least 70 wt. %, even more preferentially at least 80 wt. % and most preferentially at least 90%. It can be that 99.9 wt. % of said one or more molecular sieves are in their hydrogen form as based on the total weight of the one or more molecular sieves.

With preference, one step of steaming is carried out before step (c) at a temperature ranging from 400° C. to 1000° C., preferentially at a temperature ranging from 600° C. to 800° C. Steaming allows for the removal of a large fraction of aluminium from the lattice, which subsequently leads to an adjustment of the Si/Al atomic ratio.

With preference, the catalyst composition is calcinated before said step (c) of contacting the feedstream; with preference, the catalyst composition is calcined at a temperature of at least 400° C.

With preference, one or more of the following embodiments can be used to better define the step (a) of the process:

The one or more methyl halides in the feedstream of step (a) comprise one or more monohalo-methyl.

The one or more methyl halides in the feedstream of step (a) are or comprise methyl bromide.

The one or more methyl halides in the feedstream of step (a) comprise one or more monohalo-methyl with at most 10 wt. % of polyhalo-methyl, such as dihalo-methyl, trihalo-methyl and/or tetrahalo-methyl.

The one or more methyl halides in the feedstream of step (a) comprise a mixture of one or more selected from monohalo-methyl, dihalo-methyl, trihalo-methyl and/or tetrahalo-methyl; with preference, the mixture comprises the monohalo-methyl in an amount of at least 90 wt. % of said mixture.

The halogen of said methyl halides, or of said monohalo-methyl, dihalo-methyl, trihalo-methyl or tetrahalo-methyl is selected from fluorine, chlorine, bromine, iodine and/or any mixture thereof, preferentially bromine.

The one or more methyl halides in the feedstream of step (a) comprise at least 50 wt. % of bromine as based on the total weight of said one or more methyl halides, preferably at least 60 wt. %, more preferentially at least 70 wt. %, even more preferentially at least 80 wt. %, most preferentially at least 90 wt. %, even most preferentially 100 wt. %.

The feedstream of one or more methyl halides is diluted in a diluent, the molar ratio diluent/one or more methyl halides ranging between 2 and 20, preferentially between 3 and 10.

The feedstream of one or more methyl halides is diluted in a diluent and the diluent is gaseous nitrogen, hydrogen halides, $H_2$, $CO_2$, non-converted $CH_4$, CO, $C_2H_6$, $C_3H_8$, and/or $C_4H_{10}$, more preferably gaseous nitrogen.

In the preferred embodiment, the feedstream of one or more methyl halides contains less than 500 ppm of water and water precursor compounds (alcohols, aldehydes, carboxylic acids).

With preference, one or more of the following embodiments can be used to better define the step (c) of the process:

The reaction conditions of step (c) include a reaction temperature ranging from 220° C. to 390° C.; more preferably ranging from 280° C. to 380° C.

The reaction conditions of step (c) include a reaction temperature that is below 390° C., preferably below 380° C.

The reaction conditions of step (c) include a weight hourly space velocity of said one or more methyl halides comprised between 0.1 $h^{-1}$ and 100 $h^{-1}$, preferably comprised between 1.0 $h^{-1}$ and 15 $h^{-1}$, more preferably comprised between 1.5 $h^{-1}$ and 10 $h^{-1}$, even more preferably comprised between 2.0 $h^{-1}$ and 6.0 $h^{-1}$.

The reaction conditions of step (c) include a pressure ranging from 10 kPa to 500 kPa, preferably ranging from 20 kPa to 300 kPa, more preferably ranging from 50 kPa to 200 kPa.

The step (c) of contacting the feedstream with the catalyst composition is followed by a step (d) of recovering an effluent comprising C3-C6 olefins, one or more hydrogen halides, unreacted one or more methyl halides, alkane and higher hydrocarbons and optionally said diluent; wherein the selectivity to C3-C6 olefins is of at least 25%; with preference, of at least 50%; more preferably of at least 75%.

According to a second aspect, the disclosure provides the use of a catalyst composition in a process according to the first aspect, remarkable in that said catalyst composition comprises one or more molecular sieves with Si/Al atomic ratio ranging from 2 to 18 or from 5 to 18, and wherein said one or more molecular sieves comprise a plurality of pores, wherein said pores have a shape of 8-membered ring or less.

For example, the one or more molecular sieves are selected from the group of AEI, CHA, DDR, ERI, KFI, and LEV families and any mixture thereof; with preference, the one or more molecular sieves are selected from the group of AEI and/or CHA families.

With preference, the one or more molecular sieves with a Si/Al atomic ratio ranging from 5 to 15 and/or the one or more molecular sieves are one or more zeolites.

DETAILED DESCRIPTION

For the disclosure, the following definitions are given:

Zeolite codes (e.g., CHA . . . ) are defined according to the "Atlas of Zeolite Framework Types", 6$^{th}$ revised edition, 2007, Elsevier, to which the present application also refers.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes") and branched alkanes ("iso-paraffins" or "iso-alkanes") but excludes naphthenes (cycloalkanes).

The term "aromatic hydrocarbons" or "aromatics" relates to cyclically conjugated hydrocarbon with stability (due to derealization) that is significantly greater than that of a hypothetical localized structure (e.g. Kekule structure). The most common method for determining aromaticity of a given hydrocarbon is the observation of diatropicity in the $^1$H NMR spectrum.

The terms "olefin" or "alkene" as used herein relate to an unsaturated hydrocarbon compound containing at least one carbon-carbon double bond.

The terms "mono-olefin" as used herein relates to an unsaturated hydrocarbon compound containing one single carbon-carbon double bond.

As used herein, the term "C # hydrocarbons", wherein "#" is a positive integer, is meant to describe all hydrocarbons having # carbon atoms. C # hydrocarbons are sometimes indicated as just C #. Moreover, the term "C #+ hydrocarbons" is meant to describe all hydrocarbon molecules having # or more carbon atoms. Accordingly, the expression "C5+ hydrocarbons" is meant to describe a mixture of hydrocarbons having 5 or more carbon atoms.

The symbol "=" in the term "C #= hydrocarbon" indicates that the hydrocarbon concerned is an olefin or an alkene, the notation "=" symbolizing the carbon-carbon double bond.

The term "steam" is used to refer to water in the gas phase, which is formed when water boils.

The term "alkali metal" refers to an element classified as an element from group 1 of the periodic table of elements (or group IA), excluding hydrogen. According to this definition, the alkali metals are Li, Na, K, Rb, Cs and Fr.

The term "alkaline earth metal" refers to an element classified as an element from group 2 of the periodic table of elements (or group IIA). According to this definition, the alkaline earth metals are Be, Mg, Ca, Sr, Ba and Ra.

The term "transition metal" refers to an element whose atom has a partially filled d sub-shell, or which can give rise to cations with an incomplete d sub-shell (IUPAC definition). According to this definition, the transition metals are Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Ac, Rf, Db, Sg, Bh, Hs, Mt, Ds, Rg, and Cn. The term "transition metal" includes the group 12 elements i.e. Zn, Cd and Hg.

The yield to particular chemical compounds is determined as the mathematical product between the selectivity to said particular chemical compounds and the conversion rate of the chemical reaction. The mathematical product is expressed as a percentage.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The present disclosure provides a process for converting one or more methyl halides to acyclic C3-C6 olefins, said process comprising the following steps:
a) providing a feedstream comprising one or more methyl halides;
b) providing a catalyst composition; and
c) contacting said feedstream with the said catalyst composition under reaction conditions;

according to the disclosure, said reaction conditions include a reaction temperature below 400° C., and said catalyst composition comprises one or more molecular sieves with a Si/Al atomic ratio ranging from 2 to 18 or from 5 to 18, and wherein said one or more molecular sieves comprise a plurality of pores, wherein said pores have a shape of an 8-membered ring or less and further wherein one or more molecular sieves have an average pore size diameter of at most 4.2 Å, as determined by BET (Brunauer-Emmet-Teller) experiments.

The one or more molecular sieves are selected from one or more silico aluminophosphates and/or one or more zeolites; preferably, the one or more molecular sieves are one or more zeolites.

The one or more molecular sieves are selected from the group of ABW, ACO, AEI, AEN, AFN, AFT, AFV, AFX, ANA, APC, APD, ATN, ATT, ATV, AVL, AWO, AWW, BCT, BIK, BRE, CAS, CDO, CHA, DDR, DFT, EAB, EDI, EEI, EPI, ERI, ESV, ETL, GIS, GOO, IFY, IHW, IRN, ITE, ITW, JBW, JNT, JOZ, JSN, JSW, KFI, LEV, LTA, LTJ, LTN, MER, MON, MRT, MTF, MWF, NPT, NSI, OWE, PAU, PHI, POR, RHO, RTE, RTH, RWR, SAS, SAT, SAV, SFW, SIV, SWY, THO, TSC, UEI, UFI, VNI, YUG, and ZON families and any mixture thereof. The molecular sieve from the AEI family is SSZ-39. The molecular sieve from the CHA family is SSZ-13. The molecular sieve from the AFX family is SSZ-16. The molecular sieve from the LEV family is SAPO-35.

For example, the one or more molecular sieves are selected from the group of AEI, CHA, DDR, ERI, KFI, and LEV families and any mixture thereof; with preference, the one or more molecular sieves are selected from the group of AEI and/or CHA families.

For example, the molecular sieves from the AEI family are one or more of SSZ-39, ALPO-18 or SAPO-18, preferably SSZ-39. For example, the molecular sieves from the CHA family are one or more of chabazite, SSZ-13, SAPO-44, SSZ-62 or SAPO-34, more preferably SSZ-13. For example, the molecular sieves from DDR family are one or more of ZSM-58 or Sigma-1. For example, the molecular sieves from the ERI family are one or more of erionite or UZM-12. For example, the molecular sieve from KFI family is ZK-5. For example, the molecular sieves from the LEV family are one or more of SAPO-35, levyne, ZK-20, SSZ-17 or NU-3.

To provide an appropriate acidity, it is preferred that the one or more molecular sieves are at least partly in their hydrogen form. Preferably more than 50 wt. % of the total amount of the one or more molecular sieves used are in their hydrogen form, preferably at least 80 wt. %, more preferably at least 90 wt. %, and even more preferably 99.9 wt. % of the one or more molecular sieves are in their hydrogen form.

The one or more molecular sieves used in the catalyst composition of the disclosure have a Si/Al atomic ratio ranging from 2 to 18, preferably from 5 to 18 or from 5 to 15. This can be obtained by performing a step of steaming the one or more molecular sieves before the contact of the catalyst composition with the feedstream, namely before step (c). The steaming step allows to adjust the Si/Al atomic ratio in the samples and sometimes to avoid using a very expensive organic template. Thus, the steaming step can be used to stabilize the catalyst composition.

Moreover, less aluminium also contributes to low coke formation and low ageing rates. However, a certain amount of Al in the framework is important for the catalyst activity. Sometimes, the steaming could also eliminate the non-selective sites (non-paired sites). In this case, the sample subjected to the steaming could be preliminary exchanged with a bivalent cation ($Cu^{2+}$, $Co^{2+}$, $Ca^{2+}$, $Mg^{2+}$) followed by steaming and back ion-exchange to protons/ammonia forms.

Steaming can be performed at a temperature preferably comprised between 400° C. and 1000° C., more preferably comprised between 600° C. and 800° C. The steaming treatment is carried out in 10-95% steam inside a horizontal quartz tube oven, during a period ranging from 0.01 h to 200 h, preferably during a period ranging from 0.1 h to 24 h, at a steam pressure comprised between 0.1 bar to 10 bar. Afterwards, the samples were optionally dried in a nitrogen flow.

The catalyst subjected to steaming could be in a powder form or a shaped form.

Steaming, in addition to trigger aluminium leaching, also allows for the reduction of the number of acid sites.

In a preferred embodiment, the catalyst composition may contain one or more alkaline earth metal-containing materials. Said alkaline earth metal-containing material is selected from the group of beryllium, magnesium, calcium, strontium, barium, and any mixtures thereof.

In an embodiment, the one or more molecular sieves after or before steaming are doped with a phosphorus-containing material, to form a phosphate molecular sieve. The phosphate molecular sieve can be preferably further subjected to steaming. The catalyst composition can thus comprise between 0.1 wt. % and 7.0 wt. % of a phosphorus-containing material as based on the total weight of the catalyst composition, preferably between 0.3 wt. % and 4.5 wt. %, preferentially between 0.5 wt. % and 4.0 wt. %, more preferentially 2.0 wt. %.

The one or more molecular sieves can be doped with phosphorus-containing materials and with one or more alkaline earth metal-containing materials, preferably a magnesium or calcium-containing material. In this embodiment, the calcium and magnesium are strongly bound with phosphorous and less prone for the formation of bromides. However, the presence of the alkali earth metals on the initial molecular sieve is highly undesirable. Typically, the catalyst composition of the present disclosure comprises between 15 wt. % and 35 wt. % of a binder as based on the total weight of the catalyst composition.

With preference, the one or more molecular sieves are transition metal-free and/or alkali metal-free.

Figure 2:
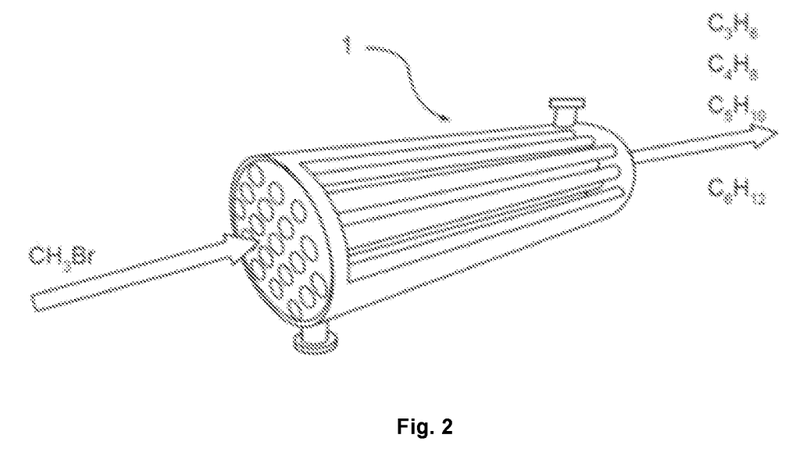
FIG. 2 schematically illustrates a fixed-bed tubular reactor in which the catalytical reaction of the present disclosure is carried out.

When the catalyst is ready, the catalyst is filled in a reactor, which can be a fixed bed, a fluidized bed or another suitable reactor. Preferentially, it can be a fixed-bed tubular reactor 1 as schematically shown in FIG. 2. In this case, the diameter of the inner tube may be of 11 mm.

With preference, the catalyst is pre-activated before the step of contacting the feed. The pre-activation is a step of calcination and is performed at high temperature, preferably between 500° C. and 550° C. The molecular sieve is preferably calcinated for at least 5 hours, preferentially for at least 6 hours. The molecular sieve is calcinated before the step of contacting in a nitrogen atmosphere. The step of calcination provides for a crystalline structure to the molecular sieve.

Optional Modification of the Phosphorous Modified Steamed Catalyst

The catalyst composition modified with a phosphorous containing-material may contain a metal-containing material, which is preferably an alkaline earth metal-containing material. However, the alkaline earth metal-containing material is spatially separated from the molecular sieve, in which alkaline earth metal is strongly bounded with phosphorous. The said alkaline earth metal is selected from the group of beryllium, magnesium, calcium, strontium, barium and any mixtures thereof.

The metal-containing material that can be added to a catalyst composition modified with phosphorous is advantageously in the form of alkaline earth metal salts and comprise at least one inorganic anion selected preferably from the group of oxides, silicates, aluminates, titanates, phosphates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{3-}$, $B_2O_5^{4-}$, $B_4O_7^{2-}$, $B_6O_{11}^{4-}$, $B_{10}O_{19}^{8-}$ and so on. Suitable aluminate anions include $Al_2O_4^{2-}$, $AlO_4^{5-}$, $Al_6O_{18}^{18-}$ and so on. Suitable titanate anions include $TiO_3^{2-}$, $Ti_3O_7^{2-}$, $Ti_4O_9^{2-}$, $TiO_4^{4-}$ and so on. Suitable phosphate anions include $PO_4^{3-}$, $HPO_4^{2-}$, $H_2PO_4^-$, $P_nO_{3n+1}^{(n+2)-}$ and so on. Bi-, tri- and poly-metal silicates, borates and borosilicates containing one, two or more alkaline earth metals selected from the list above can be used too. The metal salt may also comprise other anions.

Examples of suitable alkaline earth metal salts that can be added to a catalyst composition modified with phosphorous include $Mg_6Al_2CO_3(OH)_{16}.4(H_2O)$ (hydrotalcite), $Mg_2B_2O_5.H_2O$, $CaMgB_6O_{11}.6H_2O$ (hydroboracite), $Ca_2B_6O_{11}.5H_2O$ (colemanite), $Ca_4B_{10}O_{19}.7H_2O$, $Mg(BO_2).8H_2O$, $Ca(BO_2).2H_2O$, $BaB_6O_{10}.4H_2O$, $CaSi_6O_{17}(OH)_2$ (xonotlite), $CaMg(Si_2O_6)_x$, $Mg_2(Si_2O_6)_x$, $CaAl_2Si_2O_8$, $Mg_4Si_6O_{15}(OH)_2.6H_2O$ (sepiolite), $(Mg,Al)_2Si_4O_{10}(OH).4H_2O$ (palygorskite or attapulgite) and mixtures thereof.

A further example of suitable alkaline earth metals that can be added to a catalyst composition modified with phosphorous is $Mg(NO_3)_2$ (magnesium nitrate).

Before mixing with the molecular sieve, said alkaline earth metal salts may be modified by calcination, steaming, ion-exchange, impregnation, and/or phosphatation. Said alkaline earth metal salts can be an individual compound or can be a part of mixed compounds, for example, mixed with mineral, natural or chemical fertilizer.

In a preferred embodiment, the catalyst composition modified with phosphorous further comprises from 1 to 50 wt. % of hydrotalcite as based on the total weight of the catalyst composition; with preference from 5 to 25 wt. %, preferably from 7 to 23 wt. %, even more preferably from 10 to 20 wt. %. The hydrotalcite is of the formula $Mg_6Al_2CO_3(OH)_{16}.4(H_2O)$.

In another preferred embodiment, the one or more molecular sieves are doped with both at least one phosphorus-containing material and with at least one alkaline earth metal-containing material, preferably at least one magnesium-containing material and/or at least one calcium-containing material.

The Shaping of the Catalyst with a Binder

According to the disclosure, one or more molecular sieves are shaped with a binder, which is an inorganic material, and preferentially silica. The molecular sieves shaped with the binder forms a catalyst composition, and the catalyst composition of the present disclosure preferably comprises at least 10 wt. % of a binder based on the total weight of the catalyst composition; with preference at least 50 wt. %.

In an embodiment, the binder is present in an amount of at least 15 wt. % as based on the total weight of the catalyst composition; preferably, in an amount of at least 20 wt. %, most preferably in an amount of at least 30 wt. %, even more preferably in an amount of at least 40 wt. %, and most preferably in an amount of at least 50 wt. %.

In one embodiment, the one or more molecular sieves are shaped with a binder, which is an inorganic material. The preferred binder is selected from silica, alpha-alumina, clays, alumina phosphates, calcium phosphates, magnesium phosphates, mullite and any mixture thereof. Most preferentially, the binder is silica.

The binder preferably does not contain any aluminium compounds, such as alumina. This is because as mentioned above the preferred catalyst for use in the disclosure is de-aluminated by steaming to increase the Si/Al atomic ratio of the crystalline silicate. The presence of alumina in the binder, as well as the presence of hydrogen halides, may lead to the re-alumination of the molecular sieve. The presence of aluminium in the binder would also tend to reduce the olefins selectivity of the catalyst and to reduce the stability of the catalyst over time.

Non-limiting examples of silicon sources suitable for the binder of the catalyst composition include silicates, precipitated silicas (for example, Zeosil® available from Rhodia), fumed silicas (for example, Aerosil®200 available from Degussa Inc., New York, N.Y.), silicon compounds (such as tetraalkyl orthosilicates, for example, tetramethyl orthosilicate (TMOS) and tetraethylorthosilicate (TEOS)), colloidal silicas or aqueous suspensions thereof (for example Ludox® HS-40 available from E.I. du Pont de Nemours, Wilmington, Del.), silicic acid, alkali-metal silicate, or any combination thereof.

Other suitable forms of amorphous silica include silica powders, such as Ultrasil® VN3 SP (commercially available from Degussa).

Other non-limiting examples of a suitable solid silica source are special granulated hydrophilic fumed silicas, mesoporous silica and high surface area precipitated silica SIPERNAT® from Evonik, Hi-Sil 233 EP (available from PPG Industries) and Tokusil (available from Tokuyama Asia Pacific).

Also, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034DI, Levasil® 200, Nalco 1034A, Ultra-Sol 7H or NexSil™ 20A.

In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik.

The silica sols with higher $SiO_2$ content than 30 wt. % and even up to 50 wt. %, for example, W1250, W1836, WK341, WK7330 from Evonik are particularly preferred.

The preferred source of silicon is a silica sol or a combination of silica sol with precipitated or fumed silica.

In an embodiment, the binder is present in an amount of at least 10 wt. % as based on the total weight of the catalyst composition; preferably, in an amount of at least 20 wt. %, most preferably in an amount of 30 wt. %, even more preferably in an amount of at least 40 wt. %, and most preferably in an amount of at least 50 wt. %.

The Process

The process comprises the step of providing a feedstream to be contacted by the catalyst, the feedstream comprises one or more methyl halides; optionally, diluted in at least one diluent. Said diluent can be one or more of gaseous nitrogen, $H_2$, hydrogen halides, $CO_2$, steam, monocyclic aromatics (e.g. benzene, toluene and/or xylene), non-converted $CH_4$, CO, $C_2H_6$, $C_3H_8$, $C_4H_{10}$.

The temperature below 400° C., preferentially below 390° C., more preferentially below 380° C., is important to limit the thermal decomposition of the one or more methyl halides, especially methyl bromide. This is less important for methyl chloride (used often in the prior art), which is more thermally stable.

In the same time, methyl bromide is much more reactive and its transformation at lower reaction temperature on the materials according to the disclosure occurs substantially via a different to hydrocarbon pool mechanism and leads to the formation of acyclic C3-C6 olefins with a limited amount of ethylene and coke. The catalyst performance is stable and allows to implement the catalysts in cheaper reactor technology. For these reasons, it is preferred that the reaction conditions include a reaction temperature ranging from 220° C. to 390° C.; more preferably ranging from 280° C. to 380° C. In general, higher temperatures favour the conversion.

In a preferred embodiment, the feedstream contains less than 500 ppm of water and water precursor compounds such as alcohols, aldehydes, and/or carboxylic acids.

The molar ratio diluent/methyl halide is ranging between 2 and 20, preferentially between 3 and 10. A highly diluted feedstream favours a high level of conversion while a weakly diluted feedstream favours the selectivity towards the formation of C3-C6 olefins.

In a preferred embodiment, the halogen of said one or more methyl halides is F, Cl, Br, or I, preferentially Br.

The methyl halide comprised in the feedstream can optionally comprise 1, 2, 3 or 4 halogens. Advantageously, the methyl halide comprised in the feedstream comprises 1 halogen and is a monohalo-methyl. In this case, it is advantageous that the halide is a bromide.

The one or more methyl halides optionally comprise up to 10 wt. % of methyl dihalide.

With preference, the weight of feed flowing per unit of weight of the catalyst per hour (weight hourly space velocity, WHSV) is comprised between 0.1 h$^{-1}$ and 100 h$^{-1}$, preferentially comprised between 1.0 h$^{-1}$ and 15 h$^{-1}$. More preferably, WHSV is comprised between 1.5 h$^{-1}$ and 10 h$^{-1}$. Even more preferably, WHSV is comprised between 2.0 h$^{-1}$ and 6.0 h$^{-1}$. This means that the catalyst of the present disclosure can convert a weight of the feed that is superior to the amount of the catalyst present in the reactor.

Preferably, the reaction conditions of step (c) include a pressure ranging from 0.1 MPa to 2 MPa, preferably ranging from 0.2 to 1 MPa.

In an embodiment, step (c) of contacting the feedstream with the catalyst composition is followed by a step (d) of recovering an effluent comprising C3-C6 olefins, hydrogen halide, unreacted one or more methyl halides, alkane and higher hydrocarbons and optionally said diluent; wherein the selectivity to C3-C6 olefins is of at least 25%; with preference, of at least 75%.

The effluent of the reactions comprises the different products that formed in the catalytical reaction (the C3-C6 olefins, the traces of ethylene, the alkanes, the unreacted one or more methyl halides, hydrogen halide, the aromatics, and the diluent if it was employed in the reaction).

A separation step can be foreseen to isolate the different components of the effluent. For example, the separation step can be performed by distillation.

Test and Determination Methods

The conversion of the monohalo-methyl ($X_{CH_3X}$) is determined according to formula (1):

$$X_{CH_3X} = \frac{[CH_3X]^i - [CH_3X]^f}{[CH_3X]^i} \times 100 \quad (1)$$

wherein $[CH_3X]^i$ and $[CH_3X]^f$ are the molar concentration of the monohalo-methyl $CH_3X$ in the (initial) feed and the (final) effluent (or product stream) respectively.

The selectivity in methane (C1) is determined according to formula (2):

$$S_{methane} = \frac{[CH_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (2)$$

wherein the numerator is the carbon adjusted molar concentration of methane and the denominator is the sum of all the carbon adjusted molar concentration of all hydrocarbon in the effluent.

The selectivity in ethylene (C2=) is determined according to formula (3):

$$S_{ethylene} = \frac{2[C_2H_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (3)$$

wherein the numerator is the carbon adjusted molar concentration of ethylene and the denominator is the sum of all the carbon adjusted molar concentration of all hydrocarbon in the effluent.

The selectivity in propylene (C3=) is determined according to formula (4):

$$S_{propylene} = \frac{3[C_3H_4]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (4)$$

wherein the numerator is the carbon adjusted molar concentration of propylene and the denominator is the sum of all the carbon adjusted molar concentration of all hydrocarbon in the effluent.

Similar equations (not shown) are used for determining the selectivity in butylene, pentene, hexene and heptane, and also for the corresponding alkanes.

The selectivity in aromatics is determined according to formula (5):

$$S_{aromatics} = \frac{6[C_6H_6] + 7[C_7H_8] + 8[C_8H_{10}]}{[CH_4] + 2[C_2H_4] + 2[C_2H_6] + 3[C_3H_6] + 3[C_3H_8] + 4[C_4H_8] + 4[C_4H_{10}] + \ldots} \times 100 \quad (5)$$

wherein the numerator is the carbon adjusted molar concentration of aromatics (benzene, toluene and xylene) and the denominator is the sum of all the carbon adjusted molar concentration of all hydrocarbon in the effluent.

Gas chromatography was performed on Columns: DB1 (40 m, 0.1 mm, 0.4 µm) and Al$_2$O$_3$ (50 m, 0.32 mm, 5 µm) using Agilent operated by ChemStation software.

The metal content was determined by X-ray fluorescence (XRF) spectroscopy using an Orbis Micro-EDXRF spectrometer equipped with a Rh source (15 kV, 500 µA) and a silicon drift detector.

The Si/Al atomic ratio corresponds to the amount of SiO$_2$ divided by the amount of Al$_2$O$_3$ taking into account the fact there are two atoms of aluminium for one atom of silicon. The silica to alumina ratio (also stated as SAR) corresponds to the amount of SiO$_2$ divided by the amount of Al$_2$O$_3$ notwithstanding the proportion of the Si atoms over the Al atoms in the chemical formula of the molecular sieve. Therefore, the value of the SAR always corresponds to twice the value of the Si/Al atomic ratio.

Si/Al Atomic Ratio in Molecular Sieve by X-Ray Fluorescence (XRF) and Magic Angle Spinning Nuclear Magnetic Resonance (MAS NMR) of Aluminium.

The Si/Al atomic ratio in molecular sieve could be determined by a combination of the XRF elemental analysis and $^{27}$Al MAS NMR. The $^{27}$Al MAS NMR is useful to determine which fraction of the alumina is in the extra framework position.

Before the acquisition of $^{27}$Al MAS spectra, the samples were hydrated in 100% relative humidity (RH) in a closed vessel filled with pure water for 24 hours (at least) to equilibrate the molecular sieve structure (a symbol H is added at the end of the number). This procedure allows reconstructing the missing OH groups (missing bonds, loose coordination of Al) thus diminishing the quadrupolar constant of $^{27}$Al. Finally, the quantity of non-observable $^{27}$Al by NMR is reduced. The 15 kHz $^{27}$Al magic angle spinning (MAS) NMR spectra were registered on Bruker Avance III HD 500 MHz (the magnetic field is 11.7 T) equipment using the broadband MAS probe using 4 mm outer diameter rotors at the spinning speed of 15 kHz (operating frequency is 130.31 MHz). The pulse sequence contained one single excitation pulse of 0.5 μs (π/8) duration (pulse nutation frequency 54.3 kHz), the interpulse delay was 0.5 s, the number of transients was 4096.

Figure 3:
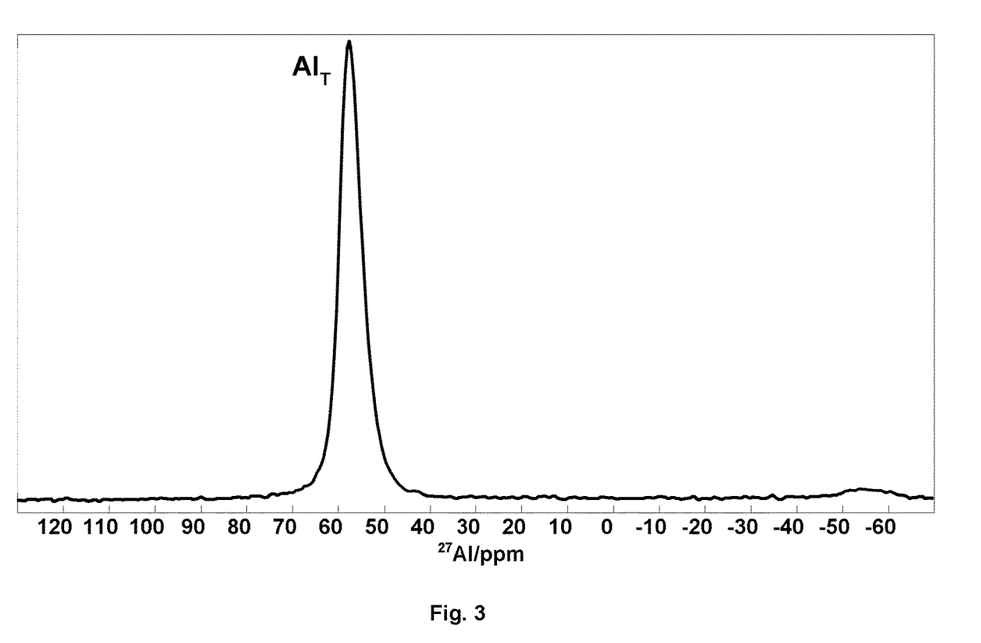
FIG. 3 shows the $^{27}Al$ MAS spectrum of SSZ-13, which is equivalent to the $^{27}Al$ MAS spectrum of SSZ-39.

FIG. 3 shows the $^{27}$Al MAS spectrum of SSZ-13, which is equivalent to the $^{27}$Al MAS spectrum of SSZ-39. The signal at 55-60 ppm corresponds to the framework of tetrahedrally coordinated Al. As there are no signals visible at 0 ppm, it means that there is not extra-framework aluminium. With this information, by performing elemental analysis with X-Ray fluorescence (XRF) experiments, it is thus possible to determine the Si/Al atomic ratio of the molecular sieve framework $(Si/Al)_{fr}$.

$$(Si/Al)_{fr} = (Si/Al) \text{ elemental analysis} * (I_{57} + I_0)/I_{57} \quad (6)$$

wherein
 (Si/Al) elemental analysis is the ratio of the content of Si and the content of Al as determined by XRF;
 $I_{57}$ is the $^{27}$Al MAS NMR peak intensity at δ of 57 ppm; and
 $I_0$ is the $^{27}$Al MAS NMR peak intensity at δ of 0 ppm.

In this case, as there is no extra-framework aluminium, the Si/Al atomic ratio of the molecular sieve corresponds to the data obtained from the elemental analysis.

The sample for the XRF is under the form of pearl, obtained from a calcined molecular sieve. The calcination temperature for the XRF experiments is 900° C. A correction based on LOI (Loss Of Ignition) has been performed to remove any volatile compounds that might interfere with the determination of elemental analysis of the sample. AXIOS instrument has been used to measure the content of Si and Al by XRF.

EXAMPLES

The embodiments of the present disclosure will be better understood by looking at the different examples below.

Example 1

Example 1A: A catalyst composition comprising steamed SSZ-39 molecular sieve having Si/Al atomic ratio of 10 (no extra framework Al) was prepared. SSZ-39 molecular sieve was steamed to form a molecular sieve having Si/Al atomic ratio of 10 (SAR of 20).

Example 1B: A catalyst composition comprising steamed SSZ-13 molecular sieve having Si/Al atomic ratio of 2.8 (no extra framework Al) was prepared. SSZ-13 molecular sieve was steamed to form a molecular sieve having Si/Al atomic ratio of 2.8 (SAR of 5.6).

Each catalyst composition was used as a catalyst for $CH_3Br$ conversion in a fixed-bed tubular reactor at a temperature of 340° C. for a period of 48 h or longer. For the catalytic test, the powder was pressed, then crushed and seized between 35-45 mesh screens. In the test, a fresh load of the seized catalyst of 10 mL (i.e. 6.3 g) was loaded in a reactor (11 mm inner diameter) and the catalyst was preactivated in an $N_2$ flow at 525° C. for 6 h. Then, the temperature was decreased to 340° C. and pure $N_2$ flow was replaced with the flow of $N_2/CH_3Br$ 10/1 mol. with WHSV of $CH_3Br$/catalyst of 1.6 h$^{-1}$. The reactor pressure was 2 barA during the test run. (2 barA means that there is a difference of 2 bar (2·10$^5$ Pa) relative to the absolute vacuum).

The results are reported in table 1 and compared to prior art results given in US2017/0057886.

TABLE 1

Conversion and selectivity results: example 1 vs. prior art

| | Example 1A | Example 1B | Comparative Example 1 [(1)] |
|---|---|---|---|
| | Catalyst | | |
| | SSZ-39 | SSZ-13 | SSZ-13 |
| SAR | 20[†] | 5.6 | 40 |
| Si/Al atomic ratio | 10 | 2.8 | 20 |
| Temperature (° C.) | 340 | 340 | 450 |
| Pressure | 3 barA | 3 barA | 1 barA |
| Partial pressure of $CH_3X$ | 0.30 | 0.30 | 0.25 |
| WHSV (h$^{-1}$) | 1.6 | 1.6 | 0.8-3.0 |
| $N_2/CH_3Br$ (mol/mol) | 10/1 | 10/1 | — |
| $N_2/CH_3Cl$ (mol/mol) | — | — | 4/1 |
| Product | Selectivity (%) | | |
| methane | <0.05 | <0.05 | n.d. |
| ethane | <0.01 | <0.01 | <2 |
| C3 | 0.6 | 0.7 | |
| C4 | 1.6 | 0.4 | |
| C5 | <0.05 | 0.2 | 0 |
| C6 paraffins | <0.01 | <0.01 | 0 |
| C6= | 12.6 | 8.8 | 0 |
| C5= | 22.9 | 11.3 | |
| C4= | 10.8 | 9.8 | <15 |
| C3= (propylene) | 32.8 | 44.3 | 33.99 |
| C7 + unsaturated hydrocarbons | 9.9 | 1.6 | 0 |
| Bromides | 0.6 | 2.4 | n.d. |
| Aromatics | 2.5 | <0.01 | <1 |
| C2= (ethylene) | 5.6 | 20.5 | 34.95 |
| C3=/C2= ratio | 5.86 | 2.16 | 0.97 |
| Total selectivity to C3-C6 olefins | 79.1 | 74.2 | <48.99[(2)] |
| Total selectivity to alkanes | <2.36 | <1.4 | <2 |
| Conversion | 50 | 30 | 98.93 |
| Stability | >24 hours | >24 hours | <1 hour |

[†]as defined from X-Ray Fluorescence (XRF) and $^{27}$Al MAS NMR; or from Si/Al elemental analysis and $^{29}$Si MAS NMR
[(1)] Comparative Example 1 corresponds to example B of US2017/0057886.
[(2)] data for C3-C4 olefins only, since higher compounds are not generated.

From the results, it can be seen that the molecular sieve catalyst SSZ-39 from the AEI family and the molecular sieve catalyst SSZ-13 from the CHA family, both having a plurality of pores with a shape of an 8-membered ring or less and the process of the disclosure achieve a high selectivity to C3-C6 olefins (79.1% and 74.2%, respectively) whereas, in the prior art, no production of higher olefins was observed, leading to a significant drop in the production of C3-C6 olefins (less than 49%).

Moreover, it was possible to restrain the generation of ethylene, as demonstrated by the propylene/ethylene molar ratio (C3=/C2=ratio) which is superior to 1 in examples 1A and 1B, while said ratio is inferior to 1 in the comparative example.

As the bond C—Br in $CH_3Br$ is weak, due to the softness of the bromine atom, it is possible to convert $CH_3Br$ into hydrocarbons on a catalyst at lower temperature than the one know in the art. Indeed, at temperature superior than 420° C., olefin cracking might already take place (without providing another catalyst composition as in the present disclosure), which would increase the yield of ethylene and subsequently decrease the total selectivity to C3-C6 olefins (see comparative example 1). However, at much lower operating temperature, namely at a temperature below 400° C., examples 1A and 1B have demonstrated that a higher C3=/C2=molar ratio is enabled. The lower temperatures further allow to maintain the stability of the catalysts, for period over 24 hours.

Examples 2 and 3 and Comparison with Example 1A

Example 2 was conducted using the same conditions as in example 1A, except that the velocity was increased from 1.6 h$^{-1}$ to 5.0 h$^{-1}$ and the flow of methyl bromide was increased, the ratio N$_2$/CH$_3$Br changing from 10/1 to 10/3.

Example 3 was conducted using the same condition as in example 2, except that the temperature was decreased from 340° C. to 280° C.

Table 2 reports the results per the three examples of the disclosure.

TABLE 2

Conversion and selectivity results: examples 1 to 3

|  | Example 1A | Example 2 | Example 3 |
| --- | --- | --- | --- |
|  | Catalyst SSZ-39 | | |
| SAR† | 20 | 20 | 20 |
| Si/Al atomic ratio | 10 | 10 | 10 |
| Temperature (° C.) | 340 | 340 | 280 |
| Pressure (barA) | 3 | 3 | 3 |
| WHSV (h$^{-1}$) | 1.6 | 5 | 5 |
| N$_2$/CH$_3$Br (mol/mol) | 10/1 | 10/3 | 10/3 |
| Product | Selectivity (%) | | |
| methane | <0.05 | <0.05 | <0.1 |
| ethane | <0.05 | <0.05 | <0.1 |
| C3 | 0.6 | 1.4 | 4.0 |
| C4 | 1.6 | 3.1 | 6.4 |
| C5 | <0.05 | 0.2 | 1.0 |
| C6 paraffins | <0.01 | 0.1 | 0.2 |
| Total selectivity to alkane | <2.36 | <4.9 | <11.8 |
| ethylene | 5.6 | 3.6 | 0.9 |
| C3= (propylene) | 32.8 | 30.0 | 16.6 |
| C4= | 10.8 | 14.3 | 15.6 |
| C5= | 22.9 | 21.4 | 28.6 |
| C6= | 12.6 | 19.8 | 15.6 |
| C7 + unsaturated hydrocarbons | 9.9 | 3.2 | 7.7 |
| Total selectivity to C3-C6 olefins | 79.1 | 85.5 | 76.4 |
| Aromatics | 2.5 | 1.8 | 2.7 |
| Bromides | 0.6 | 0.9 | 0.7 |
| Conversion | 50 | 15 | 8 |

†as defined from X-Ray Fluorescence (XRF) and $^{27}$Al MAS NMR; or from Si/Al elemental analysis and $^{29}$Si MAS NMR From the results, it can be seen that the increase of flow of methyl bromide allows for a better selectivity to C3-C6 olefins (85.5% instead of 79.1%). Additionally, the production of ethylene drops from 5.6% to 3.6%. By further applying a lower temperature, the quantity of ethylene can even be reduced to less than 1%, while a still elevated total selectivity to C3-C6 olefins is obtained (76.4%).

Those selectivity results are however counterbalanced by a decrease into the conversion.

The invention claimed is:

1. Process for converting one or more methyl halides to acyclic C3-C6 olefins said process comprising the following steps:
 a) providing a feedstream comprising one or more methyl halides;
 b) providing a catalyst composition; and
 c) contacting said feedstream with the said catalyst composition under reaction conditions;
the process is characterized in that said reaction conditions include a reaction temperature below 400° C., and in that said catalyst composition comprises one or more molecular sieves with a Si/Al atomic ratio ranging from 2 to 18 and wherein said one or more molecular sieves comprise a plurality of pores, wherein said pores have a shape of an 8-membered ring or less, wherein the selectivity to C3-C6 olefins is of at least 50%, wherein one or more molecular sieves have an average pore size diameter of at most 4.2 Å, as determined by BET experiments, and wherein the molecular sieve is doped with one or more phosphorus-containing materials and one or more alkaline earth metal-containing materials.

2. The process of claim 1, wherein the catalyst composition comprises one or more molecular sieves with a Si/Al atomic ratio ranging from 5 to 18.

3. The process of claim 1, characterized in that the one or more molecular sieves are selected from one or more silico aluminophosphates and/or one or more zeolites.

4. The process according to claim 1, characterized in that said one or more molecular sieves are selected from the group of ABW, ACO, AEI, AEN, AFN, AFT, AFV, AFX, ANA, APC, APD, ATN, ATT, ATV, AVL, AWO, AWW, BCT, BIK, BRE, CAS, CDO, CHA, DDR, DFT, EAB, EDI, EEI, EPI, ERI, ESV, ETL, GIS, GOO, IFY, IHW, IRN, ITE, ITW, JBW, JNT, JOZ, JSN, JSW, KFI, LEV, LTA, LTJ, LTN, MER, MON, MRT, MTF, MWF, NPT, NSI, OWE, PAU, PHI, POR, RHO, RTE, RTH, RWR, SAS, SAT, SAV, SFW, SIV, SWY, THO, TSC, UEI, UFI, VNI, YUG, and ZON families and any mixture thereof.

5. The process according to claim 1, characterized in that said one or more molecular sieves in the catalyst composition are selected from the group of AEI, CHA, DDR, ERI, KFI, and LEV families and any mixture thereof.

6. The process according to claim 1, characterized in that said one or more molecular sieves in the catalyst composition are selected from the group of AEI and/or CHA families.

7. The process according to claim 1, characterized in that said one or more molecular sieves are one or more of SSZ-39, ALPO-18 or SAPO-18 from the AEI family.

8. The process according to claim 1, characterized in that said one or more zeolites are one or more of chabazite, SAPO-44, SSZ-13, SSZ-62 or SAPO-34 from the CHA family.

9. The process according to claim 1, characterized in that said one or more molecular sieves contain less than 1000 wt. ppm of noble metal as determined by XRF and/or less than 1000 wt. ppm of transition metals as determined by XRF based on the total weight of one or more molecular sieves.

10. The process according to claim 1, characterized in that said one or more molecular sieves contain less than 1 wt. % of alkali metals as determined by XRF based on the total weight of the one or more molecular sieves.

11. The process according to claim 1, characterized in that said catalyst composition comprises one or more alkaline earth metal-containing material.

12. The process according to claim 1, characterized in that said catalyst composition comprises between 0.1 wt. % and 7.0 wt. % of one or more phosphorus-containing materials doped on the molecular sieve as based on the total weight of the catalyst composition.

13. The process according to claim 1, characterized in that said catalyst composition further comprises a binder.

14. The process according to claim 13, characterized in that said binder is present in an amount of at least 10 wt. % as based on the total weight of the catalyst composition.

15. The process according to claim 1, characterized in that the one or more methyl halides comprise at least 50 wt. % of bromine as based on the total weight of said one or more methyl halides; and/or the one or more methyl halides are methyl bromides.

16. The process according to claim 1, characterized in that said one or more methyl halides are diluted in one diluent.

17. The process according to claim 1, characterized in that said one or more methyl halides are diluted in one diluent with the molar ratio diluent/methyl halide is ranging between 2 and 20.

18. The process according to claim 1, characterized in that the one or more methyl halides in the feedstream of step (a) comprise a mixture of one or more selected from monohalo-methyl, dihalo-methyl, trihalo-methyl and/or tetrahalo-methyl.

19. The process according to claim 1, characterized in that a step of steaming is carried out before step (c) at a temperature ranging from 400° C. to 1000° C.

20. The process according to claim 1, characterized in that step (c) of contacting the feedstream with the catalyst composition is followed by a step (d) of recovering an effluent comprising C3-C6 olefins, one or more hydrogen halides, unreacted methyl halides, alkane and higher hydrocarbons and optionally said diluent; wherein the selectivity to C3-C6 olefins is of at least 74.2%.

21. The process according to claim 1, wherein the one or more methyl halides is methyl bromide.

22. The process according to claim 1, wherein the one or more alkaline earth metal-containing materials are a magnesium or calcium-containing material.

23. The process according to claim 1, wherein the one or more molecular sieves are SAPO-18, SAPO-34, or SAPO-44.

* * * * *